(12) United States Patent
Salvo

(10) Patent No.: US 7,258,689 B2
(45) Date of Patent: Aug. 21, 2007

(54) SILVER ALLOYS FOR USE IN MEDICAL, SURGICAL AND MICROSURGICAL INSTRUMENTS AND PROCESS FOR PRODUCING THE ALLOYS

(75) Inventor: Francesco Di Salvo, Palermo (IT)

(73) Assignee: Matteo Tutino, Palermo (IT)

( * ) Notice: Subject to any disclaimer, the term of this patent is extended or adjusted under 35 U.S.C. 154(b) by 45 days.

(21) Appl. No.: 10/726,100

(22) Filed: Dec. 2, 2003

(65) Prior Publication Data

US 2004/0236203 A1 Nov. 25, 2004

Related U.S. Application Data

(60) Provisional application No. 60/499,469, filed on Sep. 2, 2003.

(30) Foreign Application Priority Data

May 19, 2003 (IT) .............................. PA03A0007

(51) Int. Cl.
*A61B 18/18* (2006.01)
(52) U.S. Cl. ...................................... 606/41
(58) Field of Classification Search ............ 606/27–52; 600/393, 396
See application file for complete search history.

(56) References Cited

U.S. PATENT DOCUMENTS

| | | | |
|---|---|---|---|
| 1,970,319 A | | 8/1934 | Kern |
| 3,669,655 A | | 6/1972 | Cox et al. |
| 3,752,151 A | * | 8/1973 | Robichaud ................... 600/396 |
| 3,816,293 A | * | 6/1974 | Ueda et al. ............ 204/196.38 |
| 4,375,219 A | * | 3/1983 | Schmid ........................ 600/393 |
| 4,492,231 A | | 1/1985 | Auth |
| 4,668,840 A | * | 5/1987 | Kiyama et al. ............. 136/244 |
| 4,775,511 A | | 10/1988 | Kono et al. |
| 5,022,932 A | | 6/1991 | Yamada et al. |

(Continued)

FOREIGN PATENT DOCUMENTS

EP 0 685 565 A1 12/1995

(Continued)

OTHER PUBLICATIONS

Grabco et al.: "Microstructure and Strength Prpoerties of Germanium Microwires for Biomedical Devices", Institute of Applied Physics of Moldavian Academy of Sciences.

*Primary Examiner*—Roy D. Gibson
*Assistant Examiner*—Pete Vrettakos
(74) *Attorney, Agent, or Firm*—Ursula B. Day

(57) ABSTRACT

Alloys for medical, surgical and microsurgical instruments are proposed which comprise 0.01% to 20% by weight of germanium, from 0-25% of shallow hydrogenic and/or non-hydrogenic acceptor dopants in terms of weight ratio in relation to germanium, from 0% up to 20% by weight of one or more of the following compounds such as platinum, gold, palladium, iridium, ruthenium, osmium, rhodium, niobium, tantalum, tungsten, aluminium, silicon, hafnium, yttrium, lanthanum, zirconium with the remainder, up to 100% by weight, constituted by silver and inevitable impurities, wherein instruments from these alloys possess properties such as no capacitive impedance in relation to the electrode-tissue interface; a Far Infrared Radiation (FIR) emitting capacity when energized by any form of energy; sulfurization, corrosion and oxidation resistant and have suitable hardness for their intended use; emit anions and may possess fractal surfaces.

24 Claims, 5 Drawing Sheets
(5 of 5 Drawing Sheet(s) Filed in Color)

U.S. PATENT DOCUMENTS

| | | | |
|---|---|---|---|
| 5,037,708 A | 8/1991 | Davitz | |
| 5,658,281 A | 8/1997 | Heard | |
| 5,697,926 A | 12/1997 | Weaver | |
| 5,772,659 A | 6/1998 | Becker et al. | |
| 5,822,177 A * | 10/1998 | Popp et al. | 361/508 |
| 5,885,281 A | 3/1999 | Urueta | |
| 5,925,039 A | 7/1999 | Landingham | |
| 6,011,810 A | 1/2000 | Haller et al. | |
| 6,099,524 A * | 8/2000 | Lipson et al. | 606/41 |
| 6,132,357 A | 10/2000 | Sabuda | |
| 6,139,652 A | 10/2000 | Carrano et al. | |
| 6,206,876 B1 | 3/2001 | Levine et al. | |
| 6,290,501 B1 | 9/2001 | Grau et al. | |
| 6,293,946 B1 | 9/2001 | Thorne | |
| 6,296,637 B1 | 10/2001 | Thorne et al. | |
| 6,406,664 B1 | 6/2002 | Diamond | |
| 6,482,076 B1 | 11/2002 | Straub et al. | |
| 6,506,267 B1 | 1/2003 | Fujiyasu et al. | |
| 6,533,781 B2 | 3/2003 | Heim et al. | |
| 6,544,264 B2 | 4/2003 | Levine et al. | |
| 6,557,559 B1 | 5/2003 | Eggers et al. | |
| 2002/0010464 A1 | 1/2002 | Kirwan, Jr. | |
| 2002/0016591 A1 | 2/2002 | Levine et al. | |
| 2002/0111622 A1 | 8/2002 | Khandkar et al. | |
| 2002/0122741 A1 | 9/2002 | Prasad et al. | |
| 2002/0144956 A1 | 10/2002 | Silverstone et al. | |
| 2002/0173787 A1 | 11/2002 | Buysse et al. | |
| 2002/0187533 A1 | 12/2002 | Mross et al. | |
| 2003/0014050 A1 | 1/2003 | Sharkley et al. | |
| 2003/0018332 A1 | 1/2003 | Schmaltz et al. | |
| 2003/0050634 A1 | 3/2003 | Ellman et al. | |
| 2003/0139741 A1 | 7/2003 | Goble et al. | |
| 2003/0144653 A1 | 7/2003 | Francischelli et al. | |
| 2003/0163125 A1 | 8/2003 | Greep | |
| 2003/0181904 A1 | 9/2003 | Levine et al. | |

FOREIGN PATENT DOCUMENTS

| | | |
|---|---|---|
| GB | 2 033 425 A | 5/1980 |
| GB | 2 255 348 | 11/1992 |
| GB | 2 283 934 | 5/1995 |
| WO | WO96/22400 | 7/1996 |
| WO | WO 02/095082 | 11/2002 |
| WO | WO 03/028669 | 4/2003 |

* cited by examiner

Fig: 1

SILVER ALLOYS FOR USE IN MEDICAL, SURGICAL AND MICROSURGICAL INSTRUMENTS AND PROCESS FOR PRODUCING THE ALLOYS

CROSS-REFERENCES TO RELATED APPLICATIONS

This application claims the priority of Italian Patent Application Serial No. PA 2003 A 000007, filed May 19, 2003, pursuant to 35 U.S.C. 119(a)-(d), the subject matter of which is incorporated herein by reference.

This application claims the benefit of prior filed provisional application, Appl. No. 60/499,469, filed Sep. 2, 2003, pursuant to 35 U.S.C. 119(e), the subject matter of which is incorporated herein by reference.

FIELD OF THE INVENTION

The present invention relates to noble metal alloys, and in particular silver and/or gold alloys for use in manufacturing medical, surgical and microsurgical instruments. The present invention also relates to a method of producing such alloys on the basis of silver and/or gold metal alloys.

BACKGROUND OF THE INVENTION

Pure metals and metal alloys which are generally composed of silver, gold, platinum, brass, steel, titanium, tungsten, palladium and the like have long been used for personal ornaments, such as jewelry and similar. Likewise, such metals and alloys of such metals have also been used in the field of dental medicine, for example, dental implants. Furthermore, such alloys are particularly important in the field of medicine for use in making surgical instruments. A number of alloys have been well known in the prior art.

U.S. Publication No. 5,772,659 discloses an electrical generator which reduces the severity of exit sparking by providing a quick response to high impedance indications.

Furthermore, U.S. Pat. Publication No. 2002/0173787 discloses a bipolar electrosurgical instrument for sealing blood vesicles and demonstrates the necessity of using a no-sticking bipolar electrosurgical instrument.

In addition, U.S. Pat. Publication No. 2003/1076858 discloses an electrosurgical instrument for cutting and/or coagulating tissue and teaches the use of one or more electrode surfaces at least partially coated with tungsten disulphide.

Furthermore, U.S. Patent publication No. 2003/0163125 discloses the utilization of an active catalyst in a surface coating of an electrosurgical instrument.

Moreover, U.S. Patent publication No. 2003/0181904 discloses an electrosurgical cutting and coagulation instrument. In addition, U.S. patent publication No. 1,970,319 discloses a tarnish resisting silver alloy made from about 85-93% silver, tin and up to 4% of either cadmium, antimony, copper, zinc, manganese and nickel-chromium.

Other prior art documents include; U.S. Pat. Nos. 3,669,655; 6,296,637; 6,293,946; 6,557,559; 6,506,26; 6,206,876; EP Pat. No. 0685565; GB Pat. No 2,283,934; U.S. Pat. No. 6,290,501; U.S. Publication No. 2003/0050634; U.S. Publication No. 2002/0111622; U.S. Publication No. 2003/0144653; WO 03/028669; U.S. Pat. No. 6,544,264; GB Patent No. 2,255,348; WO 96/22400; GB Patent No. 2,033,425; U.S. Pat. No. 6,406,664; WO 02/095082; U.S. Pat. Nos. 6,168,071; 5,022,932; 5,039,479; 6,011,810; 6,290,501; 6,139,652; 5,885,281; 5,925,039; 6,482,076 6,533,781; 4,492,231; 5,037,708 4,775,511; 6,132,357; U.S. Pat. Publication No. 2002/0187533; U.S. Pat. Publication No. 2002/0014050; U.S. Pat. Publication No. 2002/0010464; U.S. Pat. Publication No. 2002/0144956; U.S. Pat. Publication No. 2003/0139741.

All of the forgoing prior art documents disclose pure metal or metal alloys and/or surgical instruments.

Use of pure or nearly pure silver and pure gold or coating of silver and gold and their alloys on core structures, such as aluminium or copper for manufacturing electro-surgical forceps and electrodes are also known from U.S. Pat. Nos. 6,293,946 and 6,296,637.

Moreover, pure silver and gold metal or nearly pure silver and gold have a Vickers hardness (HVN) of about 30 as an ingot while having a HVN of about 54 when worked into a wire. It should be understood that the hardness measure in HVN is according to ASTM Spec. E 384-73, using a 200 g load applied for 12 seconds varied as a function of the temperature at which age hardening occurs.

Alloys of pure silver and gold metal, as taught in the afore-stated patents generally possess a satisfactory hardness for medical and surgical instruments at least at the outset. However, instruments made from these metal alloys do not always retain their hardness over a course of time due to their repeated exposure to heat during the course of their use in, for example, when carrying out electro-surgery. Thus, it is very difficult to retain proper hardness over a long course of time, specifically with respect to surgical instruments. Retaining hardness in surgical instruments as referred in the above-described prior art patent documents is extremely difficult and the loss of hardness is a major drawback in this physical criteria in the afore-stated patents.

Furthermore, the prior art references do not disclose or teach any alloys that are suitable for medical, surgical and micro-surgical instruments and which possess a very low capacitive impedance with respect to an electrode-tissue interface, nor does the prior art disclose instruments that are able to emit far infrared radiation (FIR) used in the treatment of biological tissue in the medical field, specifically in the surgical field.

It would therefore be desirable and advantageous to provide improved alloys for use in the production of electrosurgical instruments in order to obviate prior art shortcomings. Such alloys should be biocompatible and should be made from a non-stick material with high electrical and thermal conductivity. Furthermore, such materials should have appropriate hardness levels suitable for intended use, for example for surgical instrumentation. In addition, the alloys should be highly resistive to tarnishing, and to oxidation and corrosion. Such alloys should also have low capacitive impedance relative to any electrode-tissue interface while carrying out electro-surgical treatments.

In accordance with the present invention, noble alloys are proposed, essentially for use in manufacturing innovative medical, surgical and microsurgical instruments which possess high thermal and electrical conductivity, which are tarnish and corrosion resistant, and which have non-stick properties, low capacitive impedance in relation to the electrode-tissue interface and are damage-proof against scratching or rubbing, and that are extremely hard, with a Vickers hardness of 32 HVN or higher and that can emit far infrared radiation.

It is understood that the alloy according to present invention has far reaching applicability in areas other than medicine and/or applications as surgical instruments and can be used in any field, for example in the computer field or in chip technology where those characteristics described below and others are desirable.

SUMMARY OF THE INVENTION

In accordance with the present invention, the proposed noble alloys have a silver and/or gold alloy basis and possess the afore-stated properties due to certain alloy components which when added to the melt renders the alloy extremely hard, as well as tarnish and corrosion resistant, and is ultra electro- and thermo-conductive and biocompatible. According to one aspect of the present invention, an alloy for use in manufacturing medical, surgical, microsurgical and electrosurgical instruments includes from 0.01% to 20% by weight of germanium; from between 0% to 25% by weight relative to the germanium of at least one of a non-hydrogenic and shallow hydrogenic acceptor dopant; up to 20% by weight of one or more of the compounds selected from the group consisting of platinum, gold, palladium, iridium, ruthenium, osmium, rhodium, niobium, tantalum, tungsten, aluminum, silicon, hafnium, yttrium; lanthanum, zirconium and a remainder up to 100% by total weight constituted by silver which includes impurities.

According to a feature of the present invention, the alloy is capable of emitting anions. Furthermore, the alloy is resistant against sulfurization and exhibits very low capacitive impedance relative to an electrode-tissue interface and is able to emit far infrared radiation for the treatment of biological tissue.

It is another feature of the present invention that the alloy contains semiconductor microcrystals in the form of p-type germanium quantum dots which renders the alloy suitable as constituent material for medical, surgical and micro-surgical instruments.

It is a further aspect of the present invention to provide a silver/gold alloy containing p-germanium microcrystals which is suitable as the constituent material for medical, surgical and microsurgical instruments.

Following are certain features of the alloy according to the present invention, for example, when the alloy is used for surgical instruments.

For example, in connection with a surgical electrode, the alloy material does not produce high capacitive impedance in relation to the electrode-tissue interface during operation modes since the electrode-tissue interface conduction is fully ohmic and interface is achieved by providing an electrode made from an alloy material having embedded within its matrix p-type germanium quantum dot, certain semiconductor microcrystals in the form of p-type germanium so that any electrical energy is conducted through movement of holes (electron vacancies) or electrons. Thus, when operating the electrode, no layer of cations is able to form within the living biological tissue surrounding the electrode and at the same time electrons do not collect at the electrode surface.

The electrode and forceps according to the present invention used as surgical instruments maintain a low electrode-tissue interface temperature which prevents an impedance rise during radio frequency application at high power. In the alloy, according to the present invention, the conduction at the electrode-tissue interface is sustained not by the solution phase ions movement but by the hole (electron vacancy) or electron movement.

Each of the metals, germanium and acceptor dopants used according to the present invention are safe materials to be used in contact with biological living tissue.

The alloy contains metals which confer upon it appropriate degrees of hardness, ductility and malleability. Germanium is known as a hardness-improving component.

The alloy can emit a large quantity of anions because germanium contained in the alloy material is a crystal having electric polarization;

The surface of the instruments made from alloys according to the present invention can have a fractal geometry for a better energy distribution;

The alloy has excellent sulfurization, corrosion and oxidation resistance even under arduous conditions.

The alloy fully exhibits the far infrared radiation effect inherent in p-type germanium nanostructured microcrystals when the germanium element is present in the alloy in a percentage from 0.9% to 9% by weight.

The alloy materials for medical, surgical and microsurgical instruments according to the present invention comprise the following acceptor dopants: copper, gallium, indium, gold, platinum, zinc, and/or their alloys. The silver alloys for medical, surgical and microsurgical instruments in accordance with the present invention comprise the following metals and elements: platinum, gold, palladium, iridium, ruthenium, osmium, rhodium, titanium, niobium, tantalum, tungsten, aluminium, silicon, hafnium, yttrium lanthanum, zirconium and/or their alloys. The alloys according to the present invention that are emitting far infrared radiation can be energized by any form of energy. That is, the energy source can be electrical energy, radio frequency energy, ultrasonic energy, laser energy, thermal energy, magnetic energy, solar energy, chemical energy, biological energy, human body energy, heat, or similar. Energy is provided to the far infrared radiation generating p-type germanium quantum dot microcrystals embedded within the alloy matrix. Upon stimulation by energy, the transitions of energy levels of the p-type germanium microcrystals are emitted in the form of electromagnetic radiation to act on living tissue cells through weak radiation. When it matches with the strong absorption band of the cell tissue, a large portion of the radiant energy carried by the electromagnetic wave is absorbed, thereby causing changes of the molecular- or atomic- or electronic-energy in the living tissue cells, which then elicits oscillations which stimulates the cell energy to thereby increase the permeability of the cell membrane. Once the living tissue cells have absorbed far infrared radiation then vibrational molecular resonance corresponding to the molecular state is caused inside the so-treated cells.

BRIEF DESCRIPTION OF THE PICTURES

The patent application file contains at least one drawing executed in color. Copies of the this patent or patent application publication with color drawings will be provided by the Office upon request and payment of the necessary fee.

Other features and advantages of the present invention will be more readily apparent upon reading the following description of currently preferred exemplified embodiments of the invention with reference to the accompanying Figures, in which.

DETAILED DESCRIPTION OF PREFERRED EMBODIMENTS

Figure 1:
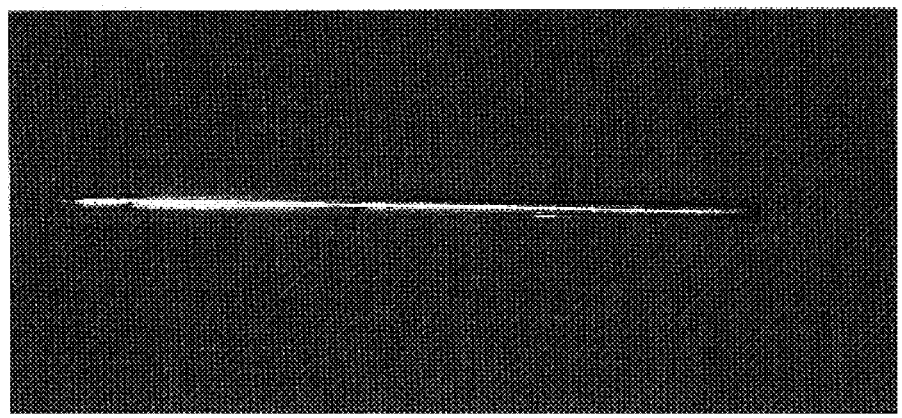
FIG. 1 is a photo of an electrode made from a silver alloy according to the present invention.

The silver alloy electrode as shown in FIG. 1 according to the present invention contains germanium for use in medical, surgical and microsurgical instruments and contains up to 20% by weight (including 0%) of one or more of the following metals and elements: platinum, gold, palladium, iridium, ruthenium, osmium, rhodium, rhenium, titanium, niobium, tantalum, tungsten, aluminium, silicon, hafnium, yttrium, lanthanum, zirconium.

Figure 3:
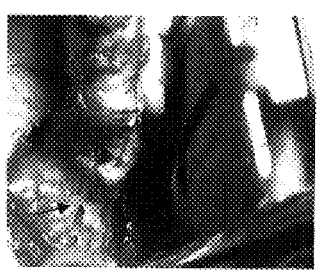
FIG. 3 is a photo showing an electrode in use during an operation showing the no-stick effect of the electrode tip.

Shown in FIG. 3 is the electrode in action during the resection of the nasal mucosal. As can be seen in FIG. 3, the electrode tip (arrow) exhibits a total absence of the "stick effect".

The silver alloy containing germanium for use in the manufacturing of medical surgical and microsurgical instruments contains from 0.01% to 20% by weight of germanium and must contain germanium in the range from at least 0.9% to 8% by weight, more specifically from 1.1% up to 5% by weight. The said silver alloy materials according to the present invention comprise at least one of the said metals and elements in addition to germanium and at least one non-hydrogenic and optionally shallow hydrogenic acceptor dopant between 0% to 25% by weight relative to the germanium. The said acceptor dopants should be present in the silver alloy containing germanium in a weight ratio, which should be no higher than 15% and no lower than 5% relative to the germanium content. According to the present invention, by melting the alloy elements, quantum dot semiconductor microcrystals ranging in dimensions between 1000 angstrom and 10 angstrom, are embedded in a metal base or alloy matrix. Electron micrographs (×18,000) have demonstrated that considerable nanometer-sized germanium microcrystal clusters are effectively formed. The minute size germanium microcrystals result in new quantum phenomena that yield some extraordinary bonuses. Hence, these minute, semiconducting microcrystal quantum dots are gateways to an enormous array of possible applications and new technologies in medical, surgical and microsurgical fields. These novel alloys represent a system with challenging new physical properties. The semiconductor is germanium and the acceptors used can be hydrogenic and/or non-hydrogenic acceptor dopants. The latter have much larger hole-binding energies than hydrogenic dopants which result in the strong reduction of the internal absorption of the generated far infrared radiation.

The non-hydrogenic dopants change the property of germanium microcrystals in the matrix of silver and at energies below the optical phonon energy where far infrared radiation occurs.

Figure 2:
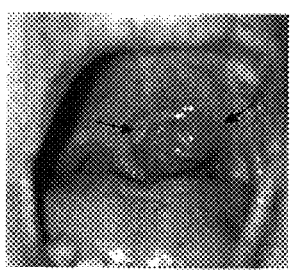
FIG. 2 is a photo showing soft palate cancer of a patient.
Figure 4:
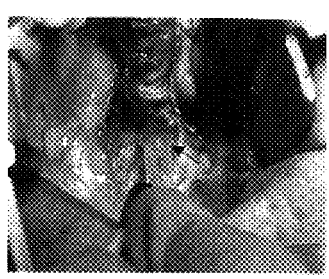
FIG. 4 is a photo showing a particular view of a muscular plain of the soft palate.

Shown in FIG. 2 is a cancer of the soft palate; the arrows point to the extension. FIG. 4 shows a view of the muscular plain resection corresponding to the elevator of the palate.

Cells are made of uniquely-arranged atoms and molecules and the molecules are all moving among and between those atoms. When molecules of mitochondria are irradiated with electromagnetic irradiation of about 100 microns wavelength band, the electromagnetic wave energy is absorbed and the amplitude of the mitochondria's molecular vibration is increased. The increased vibration produces heat through friction. When FIR (Far Infra Red), having the same vibration frequency of mitochondria, an organelle within the cell, irradiates said mitochondria, that organelle will filter out the FIR and experience a resonance absorption. This is a process known as resonance-absorption to heat-generation with aid of the FIR. The vibration of the cell atoms and molecules will generate heat and result in resonance absorption. The effects generated by far infrared radiation reduce pain sensation by direct action on both free-nerve endings in tissues and on peripheral nerves. Far infrared radiation, as a weak electromagnetic wave, has been shown to lead to both increased endorphin production and a shutting down of the "spinal gate" (Melzack and Wall), each of which reduces pain. Electrodes made with the silver alloy according to the present invention, working in an electrosurgical RF (Radio Frequency) system involve the explosive evaporation of the lymph-plasma-cytoplasm intra and inter-cellular fluids without surrounding tissue damage and generating a very clear cut. The far infrared radiation with a wavelength of 100 microns vibrates the lymphatic, plasmatic and cytoplasmatic fluids inside the cells causing resonance of the same cells and therefore their fast explosion without any spreading of heat, results in no necrosis, less bleeding, insignificant tissue oedema, zero postoperative pain, faster recovery, minimal possibility of cheloid formation, irrelevant damage to nerves and nerve endings. The thermal damage is negligible and therefore accurate and rapid biopsies can be easily performed.

Figure 5:
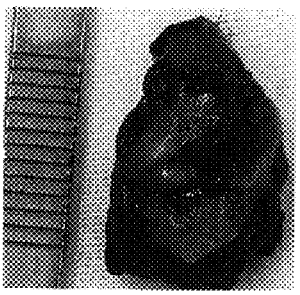
FIG. 5 is a photo showing a microscopic specimen of an area with tissue removed, wherein the edges appear smooth and the tissue well-preserved.
Figure 6:
FIG. 6 is a photo showing how an uvula flap is created without any bleeding due to the utilization of the electrode according to the present invention, characterized by a very low capacitive impedance in relation to the electrode-tissue interface and by a capacity to emit far infrared radiation.
Figure 7:
FIG. 7 is a photo showing a re-positioned flap, characterized by the total absence of thermal damage.
Figure 8:
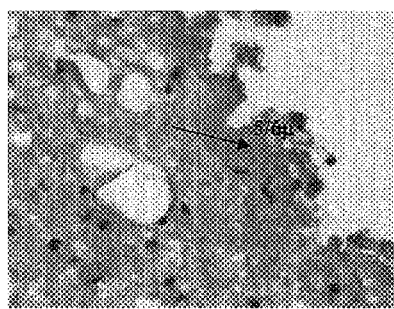
FIG. 8 is a photo showing histological connective tissue with irrelevant thermal damage (less than 6 microns)

FIG. 5 shows a macroscopic section of the cancer mass removed. To be noted are the well-preserved edges of the tissue. A uvula flap is prepared in FIG. 6 without bleeding using far infrared radiation irradiated by the electrode activated by electrothermic energy. FIG. 7 shows the flap of FIG. 6 in loco with the arrows pointing to the uvula. The absence of thermal damage or ischemia in the tissue can be observed. FIG. 8 is a histological representation of connective tissue edge of a specimen where the thermal damage is less than 6 microns (arrow).

Figure 9:
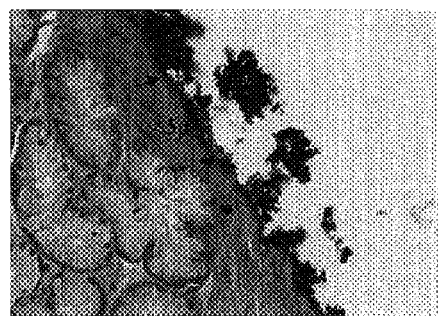
FIG. 9 is a photo showing histological glandular tissue after removal using low capacitive impedance (electrode-tissue interface) and far infrared radiation technology.
Figure 10:
FIG. 10 is a photo showing the superficial muscular plain of the palate, without any thermal damage.
Figure 11:
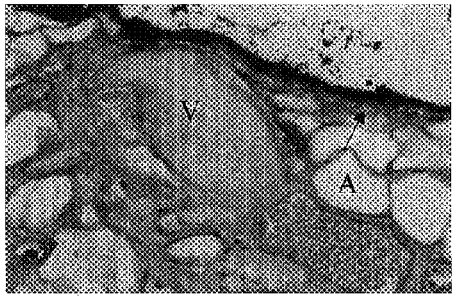
FIG. 11 is a photo showing capillaries and fatty tissues, where there is absolutely no thermal damage.
Figure 12:
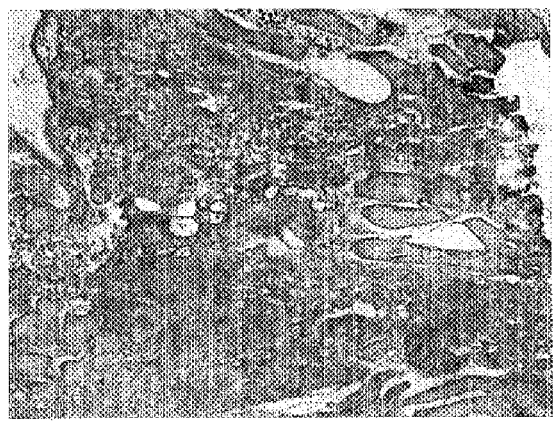
FIG. 12 is a photo showing an enlargement of 10× of histological specimen of the bottom of the implant.
Figure 13:
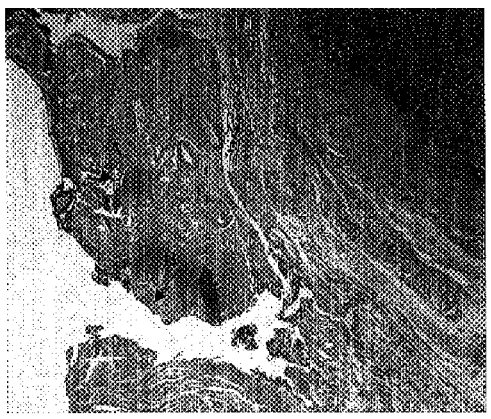
FIG. 13 is a photo showing muscular structure which remains intact without thermal damage.
Figure 14:
FIG. 14 is a photo showing the edge of a section of a superficial epithelium with irrelevant thermal damage (less than 5 microns)

FIG. 9 shows the soft-palate glandular tissue after removal using far infrared radiation technology. As shown, the edges are free of thermal damage and the glandular tissue is perfectly preserved (arrows show the edges). Absence of thermal damage is also seen in FIG. 10 and FIG. 11 with the arrow respectively pointing to the edges of the superficial section of the palate muscle. FIG. 12 is a photograph of a histology section under 10× magnifications. Focal lesions of cytoplasmic homogenization with individual cellular loss. Measured by a semi quantitative method, wherein the ratio of the thermal damage in relation to the entire surface of the fragment, the fragment is focal and ranges from 2-5% as compared to being uniform. In FIG. 13, absence of thermal damage can be seen at A-B, while the T area is affected by the cancer, a low grade polymorphic adenocarcinoma. In FIG. 14 the margin section of the superficial epithelium is shown with a thermal damage of less than 5 microns.

The coagulation is effected in an ideal fashion by denaturisation and destabilization of proteins, without burning vessels and surrounding tissue. During bipolar coagulation, the instruments according to the invention work with absolute protection of the surrounding tissues; spots and halos are not present around the tips of the forceps because the coagulation happens exclusive inside the tips of the forceps eliminating any possibility of damage to the surrounding tissues.

Figure 15:
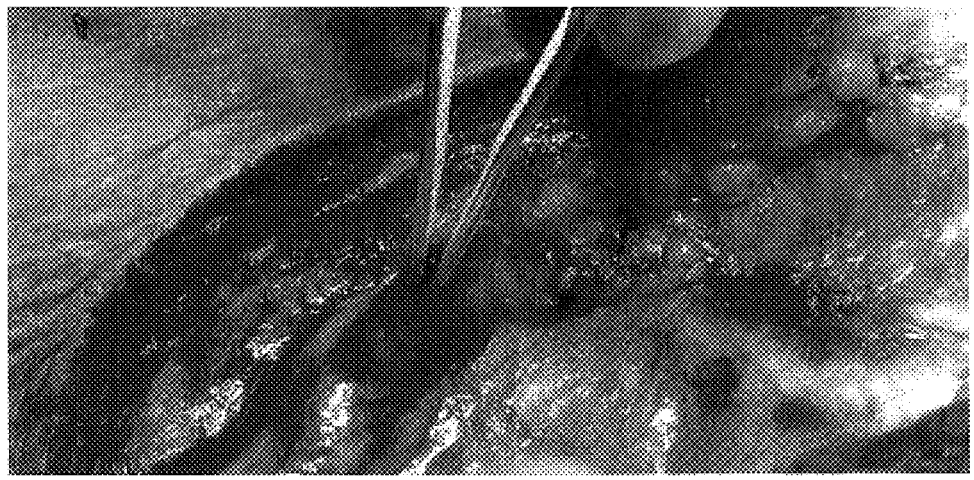
FIG. 15 is a photo showing a forceps made by the silver alloy (sample no. 4) before coagulation of a vessel.
Figure 16:
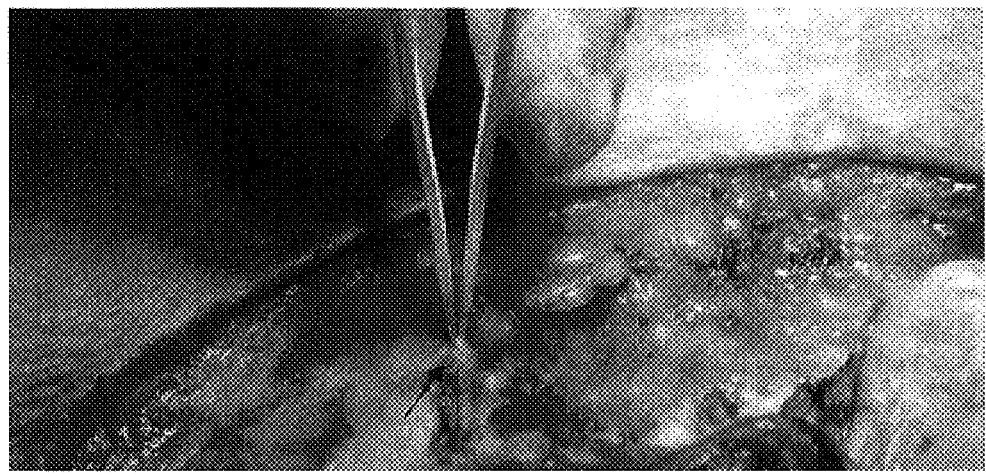
FIG. 16 is photo showing the same forceps as in FIG. 15 during coagulation.

As shown in FIG. 16 a forceps is used during coagulation in the same operation as shown in FIG. 15. The arrows indicate the precise point of coagulation which does not cause damage to the surrounding tissues. There is absolutely no "stick effect" and the temperature registered during the coagulation is below 55° C. It should be noted that the coagulation speed is much improved as compared to that attained with any other forceps currently on the market. The forceps as shown in FIG. 15 were made entirely from the silver alloy according to the present invention and are here used during the clamping of a bleeding vessel to remove cancer of the larynx and perming a neck dissection. The forceps is characterized by excellent elasticity, without damaging the vascular structures, no stick effect, precise coagulation to the point without creating thermal damage to the surrounding tissue to the vessel;

The silver alloy according to the present invention emitting far infrared radiation is configured for medical, surgical and microsurgical instruments for treating biological tissues. The term "biological tissue" refers to any living organism and any substance found within, or derived from any living organism.

The Instruments according to the present invention induce such changes because the far infrared band radiant energy delivered to the biological tissue will be converted into vibrational phonon energy at a frequency, which is the same as or related to the incident far infrared radiation. This vibrational energy in the far infrared frequency range is received, stored and re-transmitted by bio molecules, in particular by the mitochondria of the cytoskeleton. These instruments may be used to induce phonon vibrations or modify existing phonon vibrations in biological tissue. Such vibrations in the far infrared frequency of 100 microns wavelength are sustained by and can be transmitted through the cytoskeleton. Hence, far infrared radiation could be a useful approach to trigger any number intracellular processes, such as intracellular signaling. These instruments can deliver far infrared irradiation to DNA within living cells where the DNA is in the form of chromatin. These instruments can deliver far infrared radiation to centrioles within living cells or to living cells in order to modify the activity of the DNA, or can deliver far infrared radiation to living cells in order to modify the rate of DNA replication or deliver far infrared radiation to living cells in order to modify rate of DNA transcription into RNA. These so manufactured instruments can deliver far infrared radiation to DNA and centrioles within living cells in order to modify a Bose Einstein condensate of phonons in the centriole and DNA of a living cell. The instruments according to the present invention can facilitate the induction of resonant effects in some systems at a specific frequency. The optimum wavelength refers to a wavelength of far infrared radiant energy of about 80 to 120 microns and more exactly of 100 microns. This wavelength is selected for its ability to elicit the expected effect more quickly and efficiently than other frequencies, for its ability to evade absorption by hydro fluids and specifically to elicit vibrational energy in a specific article of biological tissue, or for its ability to induce vibrational energy in water molecules or chains of water molecules as a method to enhance the coupling of the far infrared radiation into a specific article of biological tissue.

The alloys of the present invention can be utilized in the following applications: medical, surgical and microsurgical fields. It can also be utilized in the following medical fields: oncology; oncological surgery; radio diagnosis and treatment; urology; ENT; cranio-maxillo facial surgery; neurosurgery; neuroradiology; neuroradiotherapy; orthopaedic surgery; orthopedics (from implants to the use of special electrodes); plastic surgery; osteogenetic distraction; cellular induction and stimulation; treatment of bedsores; aesthetic surgery; liposuction (utilizing specific cannulas which apply far infrared radiation to uniformly reduce the quantity of fatty tissue without causing thermal damage); resurfacing (application of far infrared radiation in anti-aging treatment of the face and body); synergetic application of far infrared radiation in cosmetic products; application of the electrodes emitting far infrared radiation in augmentation or reduction mammoplasty; face-neck lifts; dental implants which take advantage of the therapeutic effects of far infrared radiation to activate micro-circulation; treatment of tumors in the mouth area; treatment of cataracts; treatment of lesions in the retina; treatment of cardiopathic ischemia. Generally, but not limiting, the said invention possesses all the characteristics of being applicable to all body tissues and in the following procedures: cardio-surgery, also as implants; intravascular; arthroscopy surgery; urological, endoscopic chest surgery; laparoscopy; various heart; neurological; spinal.

EXAMPLE

The following sample alloys do not in any way constitute a limitation and are excellent for the creation of surgical and medical instruments according to the present invention: The contents (% by weight) of base metals, germanium and acceptor dopants in the cast individual samples alloys are as follows:

Sample 1: Silver-Germanium-Copper-Silicon=98:1.83:0.16:0.01

Sample 2: Silver-Germanium-Gold-Silicon=98:1.83:0.16:0.01

Sample 3: Silver-Germanium-Indium-Silicon=96:3.75:0.24:0.01

Sample 4: Silver-Germanium-Gold=98:1.85:0.15

All the materials in alloys according to the present invention can be made using conventional melting. One method for creating alloys in accordance with the present invention consists in using the process of rapid solidification (rapid cooling) utilizing a versatile combination of base metals and additives. Another method consists in effectuating melting processes in microgravity conditions. Finally, an additional method consists in melting all the components of the alloy by using high pressure. The term additive identifies germanium and acceptor dopants.

Alloys made in accordance with the present invention, be they binary, ternery quaternary, quinary or senary systems in composition yield a silver alloy material with new properties. Each alloy can be resoftened by subsequent heating and quenching to yield the alloy in its original blended state. Such a softened alloy can then be hardened again by a subsequent precipitation heat treatment. Another major characteristic of the silver alloys in accordance with the present invention is their non-toxic character. The alloy of the present invention is known to be non-toxic. The silver alloy can be a binary ternary, quarternary, quinary or senary metallic system, wherein two elements, germanium and silver are always utilized.

The contents (% by weight) of silver, germanium, copper and silicon in the cast individual sample alloy was as follows: Silver:Germanium:Gold:Silicon=98:1.83:0.16:0.01 (sample no. 2). Gold acts as a non-hydrogenic acceptor dopant. All the components are melted in a high-frequency induction furnace using argon gas. The silver alloy possesses a fusion range (solidus-liquidus) of 870° C.-890° C. The alloy is age hardened till it reaches a hardness of 120 HVN, using the following procedures:
a) heating to 700° C. for 30 minutes, and successively cooling in water.
b) treating at 250° C. for 120 minutes.

The above mentioned silver alloy contains in its matrix quantum dot p-type germanium nanostructured microcrystals and fully possesses the properties of low capacitive impedance in relation to the electrode-tissue interface and is able to emit electromagnetic far infrared radiation with the wavelength in the range of 100 microns. Said silver alloy possesses a thermal conductivity superior to 0.35 W/cm.K degrees. This characteristic is the basis for elimination of any "stick effect" on the tip of the electrosurgical instruments.

When using casting machines equipped with infrared sensing, the sensor must be calibrated for the said silver alloy as the components in the silver alloy will give a false reading because the alloy emits far infrared radiation.

The materials used in the alloy according to the present invention using the following method of fusion does not in any way constitute a limitation of the present invention: silver alloys having appropriate compositions are melted using procedures conventially known in the prior art, for example, a high-frequency induction furnace using argon gas. The final alloys are then formed in the conventional manner to obtain the final product. The alloy blend is then annealed for a predetermined period of time at elevated temperatures. The temperature for the solid solution annealing will vary with the composition of the compounds added to the silver in the alloy. The suitable annealing temperature is one which will substantially soften the alloy. A range of temperatures between 450 C-800 C is deemed to be useful. Optionally, it has been found that an annealing of 750 C for 2 hours is best for subsequently successful hardening of the annealed alloy. Pre-alloying of germanium with silver improved the product. Furthermore, while 2 hours of annealing time was considered optimum, the annealing time may be varied form 0.5 hours to 6 hours depending upon the variety and quantity of metals as well as the thickness. Subsequently, at the end of the annealing period, the solid solution of metals is rapidly cooled or quenched thereby bringing the alloy to ambient room temperature. After quenching, the alloy is preferably age hardened to obtain the precipitation hardening effect. Age hardening comprises elevating the alloy to a temperature ranging from 150 C-300 C and maintaining the alloy at this temperature uniformly for a period ranging from typically from 0.5 to 24 hours. Lab testing has demonstrated that the optimum aging time and temperature is from about 205 C to about 260 C for one hour to produce the highest hardness in the alloy for most embodiments according to the present invention. The age-hardened alloy is allowed to cool to ambient room temperature. It should be understood that the present invention comprises the making of silver alloys containing essentially germanium and optionally other metals subsequent to annealing the alloy and age-hardening the alloy. It should also be understood that the alloys according to the present invention maybe work-hardened rather than age-hardened.

The ingots are homogenized at 250° C. to 700° C. for about ½ hr to 6 hrs and are then immediately subjected to hot working at a rate of at least 30%, followed by water quenching and then milled. The alloys so obtained are subjected to cold rolling to a thickness of about 40%, and precipitate hardening and again at 250° C. to 600° C. The steps of cold working and aging may be repeated so as to obtain the desired strength and current conductivity. If necessary, the aged silver alloy in the form of strips, sheets, rods, wires, billets tubes and the like can be further subjected to a small amount of cold working; however, eventually the amount of the additional cold working should be less than 40%.

The alloys can be utilized to laminate or partially and wholly coat material cores which can be used for manufacturing said instruments.

The medical instrument can be made by coating them partially or completely with one or more of a material selected from the group consisting of biocompatible, insulating, semi-insulating elements, compounds and ceramic materials.

The alloy can also be made using conventional fusion methods and prepared by under high pressure conditions.

The alloy of the present invention can also be used to laminate, coat or be applied to any kind of conductive and non-conductive material using chemical processes. (e.g. non-electro plating) or chemical-physical processes (e.g. electroplating) or physical processes (e.g. thermal spray coating).

Clinical Cases

The following electrosurgical operative modes do not in any way constitute a limit and are excellent surgical procedures performed utilizing some instruments, such as electrodes and forceps, made using the silver alloy according to the present invention.

An operation to ablate a tumor of the soft palate of Mr. G. D., a 75-year-old male was performed in Palermo on 02.05.2003 by Dr. T. a plastic and cranio-maxillo facial surgeon. In order to perform this operation, a conventional power generator was used. The electrodes to perform the operation (FIG. 1) were made of a silver alloy material (Ag:Ge:Au:Si=98:1.83:0.16:0.1) and prepared according to the described method. Under general anaesthesia, the palatal mucosal surrounding the tumour was infiltrated to the deepest layers and an incision was performed in the healthy tissue surrounding the tumour. The incision was conducted up to the nose mucosal layer which was preserved. The tumor mass was entirely removed (FIG. 3). The loss of substance was closed by a flap of elevator muscle of the palate and uvula (FIGS. 6 and 7). The muscle plain was closed using vicryl, while nylon suture 5/0 was used for the mucosal plain. The tumor removed and the surrounding edges were sent to a laboratory for a histological exam.

Results: the patient awoke in a natural manner and from the start did not complain of any post-operative pain. There were no signs of oedema or pain in the area operated on.

Histological exams: Examination of the macroscopic specimens did not evidence thermal damage higher than 6 microns in the connective tissue. Regarding the tissue, muscle and glandular structure, thermal damage was irrelevant nor were there alterations in the structure. The subcutaneous fatty tissue and vessels were intact. In none of the above-mentioned histological exams was cellular damage caused by heat noted (FIGS. 8-14).

Other clinical cases were successfully done to date.

The following four operations were performed by the same surgeon:
1. Excision of a cancer of the soft palate;
2. Laryngectomy and neck dissection (FIGS. 15 and 16)
3. Excision of cancer of the scalp infiltrating the skull
4. Excision of cancer of the retro-molar region infiltrating the tongue where a tongue re-section, partial hemimandibulectomy and neck dissection were performed.

Office Procedures:
1. Uvulopalatoplasty (3 cases)
2. Excision of Basal Cell Cancer of the face (3 cases)
3. Excision of a cutaneous nevus (8 cases)
4. Preauricular fistula removal
5. Excision of a large, infected lipoma (8 cm×4 cm) in the gluteal region;

In all the cases performed, it was noted that during surgery the silver metal alloy materials offered the following characteristics:
1. No-stick effect of the prototype instrumentation used during cut, cut and coagulation mode;
2. No-stick effect of the forceps during coagulation mode;
3. Ohmic contact with a low capacitive impedance in relation to the electrode-tissue interface;
4. Perfect cut with irrelevant thermal damage;
5. High thermal and electrical conductivity;
6. Possess perfect conduction and have anti-corrosion/anti-oxidation properties;
7. Are completely biocompatible;
8. The silver alloy material according to the invention is far superior in quality as compared to existing materials used to make conventional medical, surgical, microsurgical and electrosurgical instruments;
9. Emission of far infrared radiation which gives the characteristics of treating biological tissue during all operative modes;
10. Perfect coagulation, without thermal damage of the surrounding tissue;
11. Rapid coagulation in comparison to any other existing instruments;
12. Extreme versatility of the instrumentation realized with this alloy.

With respect to point 9 of the above, intrasurgical emission of far infrared radiation gives the surgeon the opportunity to treat the affected area being operated on with beneficial far infrared radiation and with all related therapeutic effects used in medical, surgical, microsurgical, electrosurgical and physical therapy, orthopaedic, oncological and in all other medical fields.

The following was noted in all patients in the postoperative period: There was no post-operative pain, so pain killer or anti-inflammatory treatment was not necessary. Postoperative condition was characterized by rapid healing process without haematomas, oedema nor seromas and very high patient satisfaction.

During the various operation phases, the far infrared radiation emitted by the quantum dot p-germanium nanostructured microcrystals act in synergy with the electrothermal energy provided by the power generator and the anti-stick effect produced by the high thermal conduction of the alloy material in the presence of an irrelevant capacitive impedance due to the electrode-tissue interface. Therefore it is possible to obtain perfect cell dehydration during surgical cutting. Based on what has been said and demonstrated, it may be claimed that the germanium containing alloy materials of the present invention are the most advanced technology for selective and ablative treatments of tumors.

All the above-mentioned patents and references are thereby fully incorporated by reference and made a part of this disclosure. In the present invention, experience, studies and clinical evidence have been presented. Furthermore, hypothesis have been evidenced which attempt to explain the real and effective results of the alloy material used in the making of medical, surgical, electromedical, and microsurgical instruments applicable for humans, animals, biological and any organic elements.

The above describes the preferred forms of realization; however, other alternative forms are possible. Other forms or variations in the invention can be made by a skilled technician under the condition that said forms or variations do not change in any way the original intent of the invention. Therefore, all photos, examples and descriptions must not limit the intent of the invention which is integrated and defined by the attached Claims.

While the invention has been illustrated and described as embodied in medical, surgical and electrosurgical instruments from special metal alloys, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and their equivalents:

1. A medical instrument for use in surgical procedures made from an a silver alloy comprising from 0.9% to 3.75% by weight of germanium; from 5% to 15% by weight relative to the germanium of at least one of a non-hydrogenic and shallow hydrogenic acceptor dopant; up to 1% by weight of a compound selected from the group consisting of copper and silicon, and as a remainder up to 100% by total weight constituted by silver, and wherein the instrument is coated partially or completely with one or more of a material selected from the group consisting of biocompatible, insulating, semi-insulating compounds and ceramic materials.

2. The instrument of claim 1, wherein the said one or more material is laminated over a core material of the instrument.

3. The instrument of claim 1, wherein the instrument is produced by conventional fusion methods.

4. The instrument of claim 1, wherein medical instruments include devices selected from the group of prostheses and implants of suitable shape and size.

5. The instrument of claim 1, capable of emitting far infrared radiation upon contact with a biological tissue and which is capable of entering into molecular resonance vibration with bio structures and physical structures of so irradiated biological tissue.

6. The instrument of claim 1, capable of creating an ohmic contact in an electrode-tissue interface during electrosurgical operative modes.

7. The instrument of claim 1, wherein the alloy has a hardness in the range from 80 to 100 HVN.

8. The instrument of claim 1, wherein a p-type germanium is dispersed in the form of micro crystals in a matrix of the silver.

9. The instrument of claim 1, wherein the non-hydrogenic and the hydrogenic acceptor dopants are selected from the group consisting at least one of gold, platinum, copper, gallium, indium, zinc, boron and their alloys.

10. The instrument of claim 9, wherein the non-hydrogenic acceptor dopant is at least one of gold and copper.

11. The instrument of claim 1, wherein the weight ratio of the acceptor dopant relative to the germanium is less than 15%.

12. The instrument of claim 11, wherein the weight ratio of the acceptor dopant relative to germanium is at least 5%.

13. The instrument of claim 1, wherein the germanium is present in the form of p-type germanium microcrystal dispersed in a matrix of the alloy and capable of emitting far infrared radiation in the electromagnetic spectrum with a frequency range from 0.1 to 4 THz.

14. The instrument alloy of claim 13, wherein the p-type germanium micro crystals dispersed in the alloy matrix are capable of stimulation to an emission of far infrared radiation from a source of energy.

15. The instrument alloy of claim 14, wherein the energy is selected from the group consisting of sources of thermal energy, electro-thermal radiofrequency, body heat, ultrasound, microwave energy, laser energy, solar energy, DC current, AC current, biological energy, chemical energy.

16. The instrument alloy of claim 1, wherein the alloy is resistant to processes selected from the group consisting of sulfurization, corrosion and oxidation.

17. The instrument alloy of claim 1, having a hardness of HVN from 32 to 203 or more depending on the use thereof.

18. The instrument alloy of claim 1, wherein the alloy is capable of emitting anions.

19. The instrument of claim 1, wherein the alloy possesses fractal surfaces.

20. The instrument of claim 1, wherein the germanium containing alloy exhibits a thermal conductivity above 0.35 W/cm K. degrees.

21. The instrument of claim 1, wherein the alloy contains germanium in the range from 1.1% to 1.85%.

22. A surgical mono-or pluripolar electrode for use in surgical procedures made from an silver alloy comprising from 0.9% to 3.75% by weight of germanium; from 5% to 15% by weight relative to the germanium of at least one of a non-hydrogenic and shallow hydrogenic acceptor dopant; up to 1%-20% by weight of one or more of a compound selected from the group consisting of gold, indium, copper and silicon, and as a remainder up to 100% by total weight constituted by silver, wherein the electrode exhibits no capacitive impedance in relation to an electrode-tissue interface when coming in contact with biological tissue during electro surgery.

23. The instrument of claim 7, wherein the hardness is in the range of 40 to 149 HVN.

24. The instrument of claim 22, wherein the alloy contains germanium in the range from 1.1% to 1.85%.

* * * * *